(12) United States Patent
Brown et al.

(10) Patent No.: US 6,784,330 B2
(45) Date of Patent: *Aug. 31, 2004

(54) PROCESS FOR INTEGRATING A METHANOL CONVERSION UNIT WITH AN FCC UNIT

(75) Inventors: Stephen H. Brown, Brussels (BE); William A. Weber, Burlington, NJ (US); Reuel Shinnar, Great Neck, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/641,303

(22) Filed: Aug. 14, 2003

(65) Prior Publication Data

US 2004/0054242 A1 Mar. 18, 2004

Related U.S. Application Data

(63) Continuation of application No. 09/942,890, filed on Aug. 30, 2001, now Pat. No. 6,632,971.

(51) Int. Cl.[7] ............................................. C07C 1/207
(52) U.S. Cl. ..................... 585/331; 585/302; 585/319; 585/323; 585/324; 585/310
(58) Field of Search ................................ 585/310, 302, 585/319, 323, 324, 331

(56) References Cited

U.S. PATENT DOCUMENTS

| | | | |
|---|---|---|---|
| 3,898,057 A | 8/1975 | Moller et al. | 48/197 |
| 4,027,688 A | 6/1977 | Gruber et al. | 137/13 |
| 4,134,732 A | 1/1979 | Jackson | 422/198 |
| 4,628,066 A | 12/1986 | Bonnell et al. | 518/700 |
| 4,778,826 A | 10/1988 | Jezl et al. | 518/703 |
| 5,191,141 A | 3/1993 | Barger et al. | 585/640 |
| 5,496,859 A | 3/1996 | Fong et al. | 518/703 |
| 6,046,372 A | 4/2000 | Brown et al. | 585/640 |
| 6,632,971 B2 * | 10/2003 | Brown et al. | 585/310 |

* cited by examiner

Primary Examiner—Thuan Dinh Dang

(57) ABSTRACT

A process for treating methane-containing natural gas is provided which comprises: i) converting methane to methanol at or near a site of natural gas production; ii) transporting the methanol to a refinery remote from said site of production, said refinery producing ethylene and propylene and comprising an alkylation unit which can utilize a propylene feed; and iii) converting said methanol to gasoline boiling range fuel product and petrochemicals, including ethylene, propylene, butenes and xylenes.

9 Claims, 1 Drawing Sheet

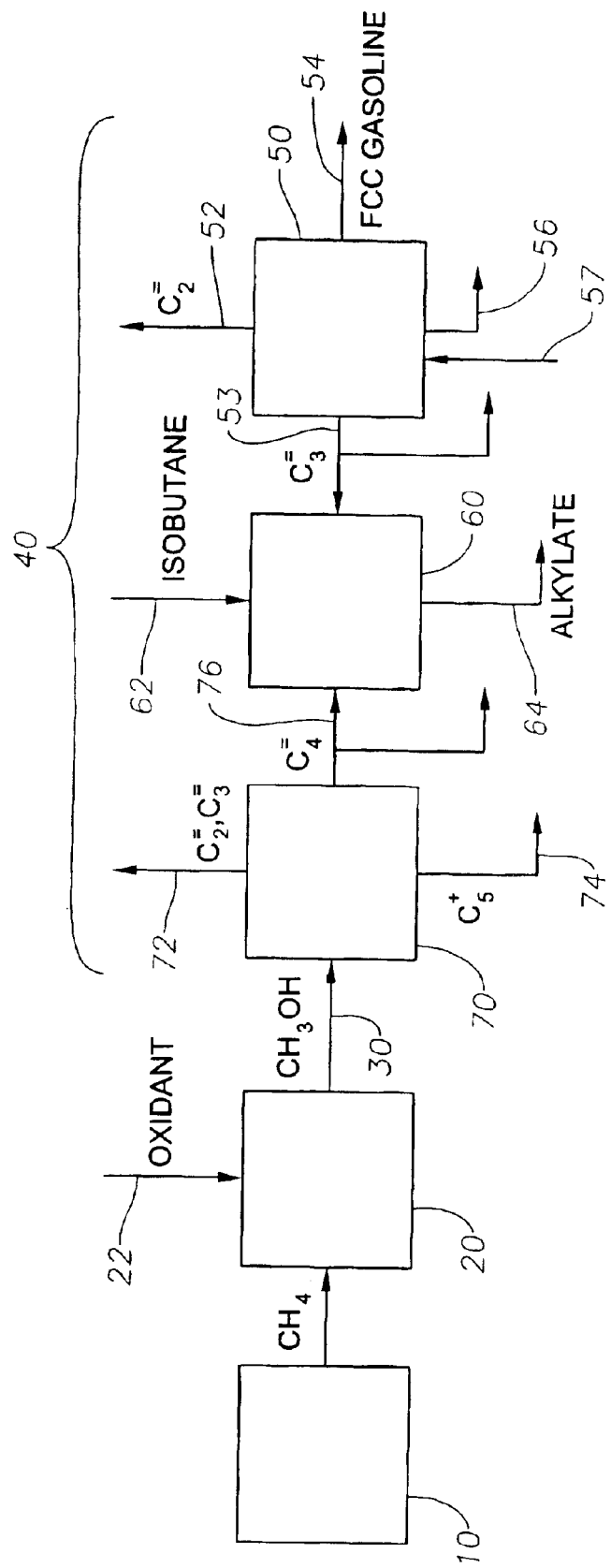

PROCESS FOR INTEGRATING A METHANOL CONVERSION UNIT WITH AN FCC UNIT

This application is a continuation of U.S. Ser. No. 09/942,890 filed Aug. 30, 2001, now U.S. Pat. No. 6,632,971.

FIELD OF THE INVENTION

The present invention relates to a process for optimizing the value of natural gas.

BACKGROUND OF THE INVENTION

The present invention is directed to a process for converting gas resources in remote locations to fuels and petrochemicals. Although the operating cost for producing fuels and petrochemicals from remote natural gas is significantly lower than producing the same products from oil, high capital costs discourage such conversion of natural gas. Reducing such capital costs would provide an incentive for utilizing natural gas as a relatively inexpensive source of fuels and petrochemicals.

Natural gas is often co-produced with oil in remote offsite locations where reinjection of the gas is either expensive or not feasible. A desirable option for treating such gas is its conversion to methanol, using Fischer-Tropsch technology, which is simpler than gas liquefaction. Methanol can be produced at reasonable cost in plants ranging from 500 to 50,000 tons a day. While larger plants have a large cost advantage, small plants are nevertheless viable if the gas cost is sufficiently negative, e.g., reinjection of natural gas is too costly or impossible. Accordingly, it has been suggested as economically feasible to place methanol plants on barges for offshore producing locations.

Despite such advantages, methanol's market is limited to only about 100 million tons per year, significantly less than that which could be produced from all natural gas sources, and therefore not suited to the scale of co-produced natural gas. However, methanol can be converted to gasoline, olefins, or a mixture of both. Indeed, a commercial plant for converting natural gas to gasoline has operated in New Zealand. Such methanol conversion processes are generally designed as integrated large-scale plants, where natural gas is converted to methanol that is then converted to hydrocarbon products.

For offshore and other difficult gas producing locations, it is preferable to provide a process, which is simple to operate. Because methanol production from natural gas is the simplest way to convert gas to liquid, it is highly desirable for on-site use. However, methanol's lack of a large-scale market militates against such conversion in the absence of a means to economically convert methanol to more readily marketable products.

U.S. Pat. No. 3,898,057 incorporated herein by reference, discloses a process for converting natural gas to a mixture of carbon monoxide and hydrogen at the site of production, converting the mixture to methanol, and transporting the methanol to a place of consumption where it is burnt or reconverted into methane.

SUMMARY OF THE INVENTION

Despite current practices, there exist certain advantages to totally separating the methanol conversion step from the production of methanol, and conducting such methanol conversion in a separate unit within a large existing refinery or in a large, dedicated methanol refinery, either of which is located in a region readily accessible to petrochemical markets, e.g., the Gulf Coast, Rotterdam, Singapore, etc.

A significant portion of costs associated with converting methanol is attributable to services or products supplied from outside sources such as steam, electricity, and fresh water. These are often available to a refinery more cheaply than at or near a natural gas producing site due to the refinery's economies of scale as well as location with respect to the supply of such services or products. In addition, gasoline product tankage and distribution infrastructure is already available at the refinery as well as facilities to handle light gas by-products.

Another reason refineries are advantageous locales for converting methanol stems from their enhanced profitability by converting methanol to gasoline as well as other higher value products as compared to solely producing a product for its fuel value as is done where methane is converted to a liquid fuel at the production site for natural gas. For example, refineries can co-produce chemicals, such as ethylene, propylene, and aromatics, having higher value than motor fuels. Moreover, the location of many refineries near petrochemical complexes or petrochemical pipelines provides a readily accessible, proximal market for such chemicals. Transporting methanol from a remote location, say, at least 10 miles, at least 20 miles or even at least 100 miles, to a refinery located near chemical markets is less expensive than transporting petrochemicals from local conversion plants for ethylene or propylene near natural gas sources. Indeed, such ethylene or propylene made near the natural gas producing site can require grassroots polymerization facilities in order to render these products transportable. In contrast, a methanol refinery located near ethylene and propylene merchant markets can readily dispose of ethylene and propylene without further processing. In general, the methanol refinery of the present invention is advantageously located where a critical mass of other refineries and petrochemical plants already exist. The methanol refinery is dependent upon a supply of low cost methanol such as that which can be economically produced from gas fields having no access by pipeline to suitably sized markets.

Decoupling gas conversion to methanol from expensive methanol upgrading processes that require investments significantly greater than the cost of the gas conversion plant provides additional benefits. Integrating methanol conversion into a refinery is particularly advantageous where the refinery can vary its product distribution according to market demand or refinery requirements. Such flexibility is lacking where methanol is converted in a remote location such as a natural gas production site.

Although a single natural gas producing site may not economically justify a methanol conversion plant in addition to methane conversion, a single methanol conversion plant could service multiple remote natural gas producing sites that transport their site-produced methanol to the plant. Such an arrangement would allow the use of a larger-scale methanol conversion plant with its attendant economies. Thus a properly situated methanol refinery would create a market for smaller natural gas producing sites that are individually unable to support individual dedicated methanol conversion plants.

According to the invention it has now been found that natural gas containing methane can be converted to higher value products by a process which comprises: i) converting said methane to methanol at or near a site of gas production; ii) transporting said methanol to a refinery remote from said site of gas production (say by at least 10 miles, at least 20 miles, at least 100 miles, or even at least 1000 miles) and proximal to petrochemical markets (say within 100 miles, preferably within 20 miles, or even more preferably within 5 miles), said refinery producing ethylene and propylene product streams and comprising an alkylation unit, e.g., one which can utilize a propylene feed; and iii) converting said methanol to gasoline boiling range fuel product and petrochemicals, such as ethylene, propylene, butenes and xylenes.

In another aspect, the present invention further comprises substituting the butenes produced from methanol for at least some of the propylene feed (producible from crude oil), in the refinery's alkylation unit to provide gasoline boiling range fuel product.

In yet another preferred embodiment, the present invention further comprises collecting individual streams of ethylene, propylene, and gasoline boiling range fuel product.

In yet another preferred embodiment, the present invention allows the refinery to produce larger quantities of gasoline low in sulfur and benzene. The $C_4$+ stream produced from methanol conversion contains very low levels of sulfur, e.g., less than 10 ppm, preferably less than 5 ppm sulfur, and more preferably no sulfur at all. Such a stream can also contain very low levels of benzene, e.g., less than 2.5 weight percent, preferably less than 1 weight percent. Blending this clean stock with gasoline fractions derived from crude oil can allow existing refineries to operate more efficiently by reducing the amount of energy and processing required to produce gasoline. A $C_4$+ gasoline boiling range product stream containing less than 10 ppm sulfur produced by the present process can be blended with a second gasoline boiling range product stream which contains at least 10 ppm sulfur to provide a gasoline boiling range product stream having a reduced sulfur content compared to said second gasoline boiling range product stream.

In another aspect, the present invention relates to a process for treating methane-containing natural gas which comprises: i) converting said methane to methanol at or near plural sites of natural gas production; ii) transporting said methanol from said plural sites to a single refinery remote from said sites of production, said refinery producing ethylene and propylene and comprising an alkylation unit; and iii) converting said methanol to gasoline boiling range fuel product and at least one petrochemical selected from the group consisting of ethylene, propylene, butenes and xylenes.

The above and other objects, features and advantages of the present invention will be better understood from the following detailed descriptions, taken in conjunction with the accompanying drawings, all of which are given by illustration only, and are not limitative of the present invention.

BRIEF DESCRIPTION OF THE DRAWING

The FIGURE depicts a process for converting natural gas to higher value products in accordance with the present invention.

DETAILED DESCRIPTION OF THE INVENTION

Methane Conversion to Methanol

The present invention contemplates the use of any suitable method for converting methane to methanol. Such a method can employ synthesis gas as an intermediate. The synthesis gas can be generated using steam methane reforming, partial oxidation or gasification, or a combined reforming or autothermal reforming process.

Steam methane reforming is the catalytic reaction of natural gas with steam to produce a synthesis gas or "syngas", which includes $H_2$, $CO_2$, CO, $CH_4$, and $H_2O$ with an $H_2$ to CO ratio of about 3:1 or higher. The steam methane reformation reaction is endothermic. Therefore, external heat is required. The natural gas and steam are typically fed into alloy tubes that contain a nickel based catalyst for the reforming reaction. The catalyst tubes are placed inside a refractory lined structure. A portion of the natural gas is used as fuel to provide the heat required for the reaction:

$$H_2O(g)+CH_4 \rightarrow 3H_2+CO$$

The drawbacks of steam methane reforming include its limitation to low pressure applications on the order of about 100–400 psig. Steam methane reforming also produces a syngas with a high $CH_4$ impurity content in a range of about 3–15 percent, and requires the external supply of $CO_2$ for methanol syngas requirements.

Partial oxidation or gasification is a non-catalytic reaction of natural gas with oxygen under controlled oxygen conditions. The reaction is exothermic as shown in the following reaction:

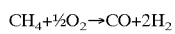

$$CH_4+\tfrac{1}{2}O_2 \rightarrow CO+2H_2$$

The partial oxidation process can be operated at high pressure to minimize or eliminate the syngas compression needed to reach the desired elevated pressure suitable for methanol production, typically about 200–2000 psig. However, the syngas produced from the partial oxidation process has a lower $H_2$ to CO ratio with little or no $CH_4$ content. Typically, the $CH_4$ varies from about 0–0.5 percent, and the $H_2$ to CO ratio varies from about 1.5–2.0. As a result, external $H_2$ would be needed to meet the methanol syngas requirements.

The combined reforming process uses a combination of conventional steam methane reforming, often referred to as "primary reforming," in combination with oxygenated catalytic reforming, often referred to as "secondary reforming," to generate stoichiometric ratioed synthesis gas for the production of methanol. See U.S. Pat. No. 4,888,130.

In a preferred aspect of the combined reforming process, a portion of the natural gas feedstock is fed to the primary reformer and the effluent is blended with the balance of the natural gas and oxygen prior to entering the secondary reformer. The drawback of the combined reforming process is that it is limited to moderate pressure applications, on the order of about 400 to 600 psig.

At higher pressures, reduced operating temperatures are necessary, and because increased amounts of $CH_4$ are present in the feed to the secondary reformer, it is more likely that soot or carbon formation will be increased. This can damage or deactivate the catalyst and lead to greater feed consumption to produce the required amount of carbon monoxide.

Most commercial methanol synthesis plants operate in a pressure range of about 700–2000 psig using various copper based catalyst systems depending on the technology used. A number of different state-of-the-art technologies are known for synthesizing methanol, and are commonly referred to as the ICI (Imperial Chemical Industries) process, the Lurgi process, and the Mitsubishi process.

The methanol syngas, also referred to as "stoichiometric ratioed synthesis gas", from the syngas generation unit is fed to a methanol synthesis reactor at the desired pressure of about 700 to 2000 psig, depending upon the process employed. The syngas then reacts with a copper based catalyst to form methanol. The reaction is exothermic. Therefore, heat removal is ordinarily required. The raw or impure methanol is then condensed and purified to remove impurities such as higher alcohols including ethanol, propanol, and the like. The uncondensed vapor phase comprising unreacted methanol syngas is recycled to the feed.

The operation of compressing the methanol synthesis gas requires expensive equipment that is costly to maintain. Moreover, the need to compress the methanol synthesis gas to reach suitable operating pressures for the methanol synthesis operation further increases the production cost of methanol. For optimal methanol production, U.S. Pat. No. 5,496,859 teaches using a stoichiometric ratioed syngas supplied to the methanol synthesis unit generally conforming to the following specifications: $(H_2-CO_2)/(CO+CO_2)=$ 1.9–2.1, and $N_2$, Ar and $CH_4 \leq 3.0\%$ and $H_2O$. This process partially oxidizes natural gas in a gasifier to produce hot pressurized syngas which is passed through a steam reforming catalytic reactor to produce a reformer syngas, a portion of which is recycled as feed to the gasifier while the remaining portion is combined with partially cooled gasifier syngas exiting the catalytic reactor to form a stoichiometric ratioed syngas. The ratio adjusted syngas then enters a methanol synthesis unit at conditions necessary to convert it to methanol with little or no external compression.

Transportation of Methanol to Methanol Refinery

Methanol is shipped from the synthesis plant to the methanol conversion refinery by any suitable means such as dedicated large tankers, supertankers or pipelines. The cost to ship is expected to be similar to the cost of shipping crude oil.

Methanol Conversion to Gasoline Boiling Range Hydrocarbons and Petrochemicals

U.S. Pat. No. 6,046,372 incorporated herein by reference, provides many examples using modified medium pore zeolite catalysts, e.g., a shape-selective crystalline silicate catalyst selected from the group consisting of ZSM-5, ZSM-11, ZSM-12, ZSM-23, ZSM-35, ZSM-48, and MCM-22, to produce ethylene, propylene, p-xylene, and gasoline precursors from methanol at commercially attractive partial pressures between 15 and 170 psia. The reference teaches that ethylene+propylene selectivity is optimized by using between 1 and 20 wt % toluene co-feed, ZSM-5 catalysts with $d/r^2$ values between 0.5 and 20, and temperatures between 380° and 500° C.

U.S. Pat. No. 5,248,647 incorporated herein by reference, describes the use of SAPO-34 type catalysts for the conversion of methanol or dimethyl ether to $C_2-C_5$ olefins at commercially attractive conversions of methanol exceeding 98%. The patent teaches that ethylene+propylene selectivity is optimized at temperatures between 400° and 500° C. and methanol pressures between 5 and 40 psia. The '372 and '647 referenced methanol conversion methods are especially suited to use in the present invention.

Preferably, the present invention can employ an olefin production zone containing a metal aluminophosphate catalyst selected from the group consisting of SAPO-34, SAPO-17, SAPO-18, and mixtures thereof, the catalyst being described in U.S. Pat. Nos. 4,440,871, 5,126,308, and 5,191,141 and hereby incorporated by reference.

U.S. Pat. No. 3,928,483 describes the use of shape-selective zeolites such as ZSM-5 for the conversion of methanol or dimethyl ether to gasoline. U.S. Pat. Nos. 3,911,041, 4,025,571, 4,025,575, and 4,052,479 describe the use of shape-selective zeolites in converting methanol and/ or dimethyl ether to olefins, to aromatic hydrocarbons, or to mixtures thereof. The foregoing patents are incorporated herein by reference as background material.

U.S. Pat. No. 4,499,314 incorporated herein by reference, discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 patent teaches that the increased conversion resulting from the addition of the promoter allows the use of lower severity conditions, particularly lower temperatures, which increase the yield of lower olefins (column 4, lines 17–22). Thus in Example 1 of the patent the addition of toluene as a promoter reduces the temperature required to achieve full methanol conversion from 295° C. to 288° C. while increasing the ethylene yield from 11 wt % to 18 wt %. In the Examples of the '314 patent the methanol feedstock is diluted with water and nitrogen such that the methanol partial pressure is less than 2 psia.

While the present invention contemplates the use of any suitable method for converting methanol, the above methanol conversion processes are especially well-suited to use in the present invention to provide a variety of products of enhanced value from a methane-containing natural gas feedstock.

The following examples will serve to further illustrate processes and some advantages of the present invention.

EXAMPLE 1

Conventional On-Site Conversion of Natural Gas to Methanol and Conversion of Methanol to Gasoline and Petrochemicals 11 billion pounds of methane-containing natural gas is converted to 1.5 billion pounds of polyethylene, 1.2 billion pounds of polypropylene, and 4.1 billion pounds of gasoline at a remote location near the production site of the natural gas. Polyethylene and polypropylene are required products because ethylene and propylene cannot be shipped economically. Costs are: 2 billion dollars for methanol synthesis, 0.7 billion dollars for methanol conversion, 1.5 billion dollars for a polyethylene plant, and 1 billion dollars for a polypropylene plant—representing a total project cost of 5.2 billion dollars.

EXAMPLE 2

On-Site Conversion of Natural Gas to Methanol and Remote Conversion of Methanol to Gasoline and Petrochemicals Referring now to the FIGURE, 11 billion pounds of methane-containing natural gas produced at production site 10 are contacted with oxidant 22 and converted to 15.5 billion pounds of methanol at an on-site methane to methanol conversion site 20. The methanol produced is transported by transportation means 30 to a refinery complex 40 which according to this embodiment comprises an FCC unit 50 which produces ethylene overhead via line 52, propylene+butylenes via line 53, FCC gasoline via line 54 and FCC bottoms via line 56, and an alkylation unit 60 which can utilize the propylene+butylenes as a feed along with isobutane via line 62 obtained from elsewhere in the refinery complex, to produce alkylate via line 64.

The feedstock for the FCC unit is shown by the line 57. Typical feeds to an FCC unit include without limitation relatively high boiling oil or residuum either on its own or mixed with other fractions. By way of example and without limitation, include gas oils such as atmospheric gas oil, vacuum gas oils, and coker gas oils.

The refinery complex comprises a methanol refinery 70 wherein the transported methanol from line 30 is converted in a molecular sieve based fluid bed methanol-to-olefin (MTO) unit 100 to 1.5 billion pounds of ethylene, 1.2 billion pounds of propylene, (which can be taken off vial line 72) and 4.1 billion pounds of gasoline and gasoline precursors (including 0.8 billion lbs butenes) taken off via line 74. An additional 0.8 billion pounds of propylene are freed up for sale to local merchant markets by displacement from the alkylation unit 60 by substituting butenes produced from methanol conversion via line 76. Costs are: 2 billion dollars for methanol synthesis at the remote location and 0.5 billion dollars to add the required molecular sieve based fluid bed MTO unit to the existing refinery, representing a total project cost of 2.5 billion dollars.

The Examples demonstrate that using a methanol refinery can reduce the required capital for a major gas to liquids project by as much as 50%. Current technology requires double the capital investment in order to co-produce large amounts of petrochemicals from natural gas. The present process allows co-production of large amounts of petrochemicals using only incrementally increased capital than is required for production of fuels alone.

In addition to greatly reduced capital requirements, the present process allows the synergies between methanol conversion and crude refining to be captured. These include but are not limited to the production of alkylate from MTO butenes, and the use of the MTO low sulfur C5+ stream to enable the refinery to reduce the amount of processing required to produce low sulfur gasoline from crude oil.

It is claimed:

1. A process for producing ethylene, propylene and gasoline boiling range fuel product, the process comprising the steps of
   i) providing methanol to a refinery comprising a FCC unit and an alkylation unit;
   ii) producing ethylene, propylene and butene in the FCC unit;
   iii) isolating ethylene and propylene produced in the FCC unit from butenes produced in the FCC unit;
   iv) converting the methanol to olefins comprising ethylene, propylene and butenes;
   v) isolating butenes produced in the step of converting from ethylene and propylene produced in the step of converting; and
   vi) supplying butene produced in the converting step and butene produced in the FCC unit to the alkylation unit to produce the gasoline boiling range fuel product.

2. The process of claim 1, winch further comprises collecting individual streams of the ethylene, propylene, and gasoline boiling range fuel product.

3. The process of claim 1, wherein the gasoline boiling range fuel product forms a first gasoline boiling range product stream containing less than 10 ppm sulfur.

4. The process of claim 3, which further comprises blending the gasoline boiling range product stream with a second gasoline boiling range product stream which contains at least 10 ppm sulfur to provide a mixed gasoline boiling range product stream having a reduced sulfur content compared to the second gasoline boiling range product stream.

5. The process of claim 1 wherein the step of converting the methanol is carried out by a methanol to olefin process.

6. The process of claim 1 wherein the step of converting the methanol is carried out in the presence of a shape-selective crystalline silicate catalyst selected from the group consisting of ZSM-5, ZSM-11, ZSM-12, ZSM-23, ZSM-35, ZSM-48, MCM-22, SAPO-18, and SAPO-34.

7. The process of claim 1 wherein the step of converting the methanol is carried out in the presence of a shape-selective ZSM-5 crystalline silicate catalyst.

8. The process of claim 1 wherein the step of converting the methanol is carried out in the presence of a SAPO-34 crystalline silicate catalyst.

9. The process of claim 1 wherein the converting the methanol is carried out in the presence of a SAPO-18 crystalline silicate catalyst.

* * * * *